United States Patent [19]

Johnson

[11] Patent Number: 5,026,639
[45] Date of Patent: Jun. 25, 1991

[54] METHOD TO IMPROVE MRNA TRANSLATION AND USE THEREOF FOR PRODUCTION OF PLATELET FACTOR-4

[75] Inventor: Paul H. Johnson, Menlo Park, Calif.

[73] Assignee: Nippon Mining Company, Limited, Tokyo, Japan

[21] Appl. No.: 143,731

[22] Filed: Jan. 14, 1988

[51] Int. Cl.$^5$ .................. C12N 15/67; C12N 15/03; C12N 15/12; C12P 21/00
[52] U.S. Cl. .................. 435/69.1; 435/69.7; 435/71.2; 435/172.3; 435/252.3; 435/320.1; 530/380; 536/27; 935/27; 935/45; 935/51; 935/73
[58] Field of Search .................. 435/68, 69, 70, 320, 435/252.1, 69.1, 172.3, 69.7, 71.2, 252.3, 320; 536/27; 935/45, 27, 51, 73; 530/380

[56] References Cited

U.S. PATENT DOCUMENTS 4,366,246 12/1982 Riggs .................. 435/69.1

FOREIGN PATENT DOCUMENTS 0281363 9/1988 European Pat. Off. .
WO8501067 3/1985 PCT Int'l Appl. .
8504397 10/1985 PCT Int'l Appl. .

OTHER PUBLICATIONS

Kahn et al., Methods in Enzymology 68 268–280, (1979).
Vernet et al., Gene 34 87–93, (1985).
Pugsley et al., J. Gen Microbiology, 132 2297–2307, (1986).
Modification of mRNA Secondary Structure and Alteration of the Expression of Human Interferon X1 in Escherichia Coli; Gene, 58 (1987), 77–86.
Duel, et al., (1981), Proc. Nat'l. Acad Sci U.S.A., 78L4584, "Platelet Factor 4 is a Chemotactic for Neutrophilis and Monocytes" Heemstra, V.L. (1983), Thrombosis Res 29:323.
Hiti-Harper, J. et al., (1978), Science 199:991, Platelet Factor 4: "An Inhibitor of Collagenase".
Katz, I. R., et al., (1986), Proc Nat'l Acad Sci U.S.A. 83:3491.
Protease Induced Immunoregulator Activity of Platelet Factor 4 Taylor, S., et al., (1982), Nature 297:307.
Wu, V. Y., et al., (1977), Prep Biochem 7:479.
Levine, S. P., et al., (1976), J Biol Chem 251:324, "Human Platelet Factor 4: Purification and Characterization by Affinity Chromatography".
Walz, D., et al., (1977), Throm Res 11:893, "Primary Structure of Human Platelet Factor 4".
Poncz, M., et al., (1987), Blood 69:219, "Cloning and Characterization of Platelet Factor 4 cDNA Derived from a Human Erythroleukemic Cell Line".
Waleh, N. S., et al., (1985), Proc Nat'l Acad Sci U.S.A. 82:8389–8393 "Structural and Functional Organization of the Colicin El Operon".
Brosius, J. Vectors: A Survey of Molecular Cloning Vectors and Their Uses, Rodriquez, R. L. et al., eds., (1988), 207, "Expression Vectors Employing Lambda, trp, lac, and lpp Derived Promoters".

*Primary Examiner*—Richard A. Schwartz
*Assistant Examiner*—Nancy Treptow
*Attorney, Agent, or Firm*—Lisabeth Felix Murphy

[57] ABSTRACT

The present invention provides a method to improve the expression of a poorly expressed recombinant protein, such as platelet factor 4, by constructing a gene fusion such that unfavorable secondary structure formed between the region of the messenger RNA specifying the recombinant protein and the region of the messenger RNA containing the ribosome binding site is disrupted. The gene fusion is constructed by inserting a DNA segment of sufficient length to disrupt unfavorable long-range folding interactions which render the ribosome binding site inaccesible to ribosomes thereby interfering with the translation of mRNA. The invention further provides for the expression of recombinant platelet factor 4 and provides recombinant DNA vectors and methods for the bacterial production and recovery of said platelet factor 4.

24 Claims, 6 Drawing Sheets

FIG. 1

CTAP-III mRNA
ENERGY = -72.7

```
              10
           A     A
        GUAUAUA  AACC
        CAUGUAU  UUGG G
               A      U
              20
       30        40       50        60            AA
      AGUA     G   ACUCG    U  AG GUU   UUA AAAGUC A
           UUUAUUU UUA       --  UC CAA  -  AAU UUUUAG G
           AAAUGGA AAU       GU       GU  A           GA
                         -CGG  -     80              70
                  90                      T1
                                                              S-D
      100        110       120        130
     GAAGAAA  GC UUGGA UCU GAC  A UU UACG CUG    AGC     -----U--
           CG   CG GGCCU AGA CUG AA AUGC GGC    UCG     CUAUUGAAGUU
     --------CA            U    A       U   AGAAAGUCUCA        230
             280       270       260        250         240
```

```
                                     160  U  AU
                                       UUC GGG C
                                       AAG CCC  AC
                                                170
                                              180
                                           A   A  UCCAG   U
                                          A AAC       C
                                            UUG AGGUC  U
                                              -   A   190
                                  150                AC   GCUA
                                 AUCAAAA    CU         AA UG  200
                          GUUGCA  UG  UGC ACG  -----         
                          CAACGU  AC  ACG                    
                     140      C   UC   210
                        CC AC
                        GG GC
                     AC     
                     220
```

```
                              (1)                              ↓
       10           20           30           40           50
5'-AATTCGTTAA CATGGAAGCT GAAGAAGACG GTGACCTGCA ATGCCTGTGC
   GCAATT    GTACCTTCGA CTTCTTCTGC CACTGGACGT TACGGACACG
                              (2)                              ↑

(3)                        ↓
       60           70           80           90          100
   GTTAAGACCA CTTCTCAGGT ACGTCCGCGT CACATCACTT CTCTGGAAGT
   CAATTCTGGT GAAGAGTCCA TGCAGGCGCA GTGTAGTGAA GAGACCTTCA
                              (4)                         ↑

(5)              ↓              (7)
      110          120          130          140          150
   AATCAAAGCT GGTCCGCACT GTCCGACTGC TCAGCTGATC GCTACTCTGA
   TTAGTTTCGA CCAGGCGTGA CAGGCTGACG AGTCGACTAG CGATGAGACT
              (6)                        ↑
                                      Xba I (9)
    A  160                ∇    180          190          200
   AAGACGGTCG TAAAATCTGT CTAGATCTGC AAGCTCCACT GTACAAGAAG
   TTCTGCCAGC ATTTTAGACA GATCTAGACG TTCGAGGTGA CATGTTCTTC
   T                          ∆
              (8)                                  (10)

↓              (11)
              220          230          240
   ATCATCAAAA AACTGCTGGA ATCTTAATGA CTGCAGAAGC TTG
   TAGTAGTTTT TTGACGACCT TAGAATTACT GACGTCTTCG AACTTAA-5'
                   ↑                     (12)
```

METHOD TO IMPROVE MRNA TRANSLATION AND USE THEREOF FOR PRODUCTION OF PLATELET FACTOR-4

DESCRIPTION

1. Technical Field

This invention is in the field of genetic engineering. More particularly, it relates to methods to improve expression and recovery of inefficiently expressed recombinant proteins, and to plasmid vectors for the cloning, expression, and microbial production of human platelet factor 4.

2. Background Art

Platelets are circulating blood cells that function in the normal blood-clotting mechanisms in response to vascular injury. Platelet alpha-granules secrete a number of important proteins, including platelet factor 4 (PF-4 or PF4), platelet-derived growth factor (PDGF), connective tissue-activating peptide (CTAP-III), and beta-thromboglobulin (beta-TG). Several of these proteins share substantial amino acid sequence homology. Although the biological roles of these factors are not well defined, four of their most important properties are (a) the ability to stimulate DNA synthesis and cell division, and thus to act as potent mitogenic agents; (b) the ability to stimulate a variety of metabolic activities in connective tissue cells, including glucose transport, glycolysis, prostaglandin E2 and cyclic AMP formation, hyaluronic acid and glycosaminoglycan synthesis, and formation of plasminogen activator; (c) the ability to attract cells of the immune system to sites of inflammation and to stimulate their function; and (d) the ability to bind with high affinity to sulfated glycosaminoglycans, important constituents of cell surfaces and connective tissue and mast cells.

Platelet factor 4 is a platelet-secreted protein with several biological functions, including procoagulation, antiheparin, immunoregulatory, and chemotactic activities. PF-4 has been demonstrated to be a potent chemotactic agent for monocytes and neutrophils (Deuel et al. (1981) *Proc Natl Acad Sci USA* 78:4584), to bind serotonin (Heemstra, V.L. (1983) *Thrombosis Res* 29:323), to inhibit collagenase (Hiti-Harper, J. et al. (1978) *Science* 199:991), to reverse immunosuppression in animals (Katz, I.R., et al. (1986) *Proc Natl Acad Sci USA* 83:3491), and to inhibit the growth of some tumors (Taylor, S. and Folkman, J. (1982) *Nature* 297:307). PF-4 has been isolated from both bovine and human blood and purified to homogeneity (Wu, V.Y., et al. (1977), *Prep Biochem* 7:479 and Levine, S.P., and Wohl, H. (1976), *J Biol Chem* 251:324) and its amino acid sequence and physiochemical properties have been determined (see for example, Walz, D.A., et al. (1977), *Throm Res* 11:893). Recently, the DNA sequence from cDNA derived from a human erythroleukemic cell line was disclosed by Poncz, M., et al (1987), *Blood* 69:219; this sequence encodes a full-length leader sequence of 30 amino acids preceded by an initial methionine residue and followed by the coding region for the 70 amino acid mature protein.

To date, successful production of PF-4 by recombinant DNA technology has not been reported. Moreover, unlike the success achieved with human connective tissue-activating peptide-III, a protein with over 60% homology with PF-4, similar attempts by the present inventor using PF-4 in identical expression systems have been wholly unsuccessful for the direct expression of PF-4 The PF-4 reported in the earlier studies was obtained from platelets, a method of isolation that would be impractical for generating large amounts of the protein. In this regard, one object of the present invention is to provide the means for producing PF-4 via recombinant DNA technology. These means include the use of a synthetic gene encoding PF-4 that is designed for expression of PF-4 in bacteria and expression vectors that contain the PF-4 gene fused to modified colicin El structural gene regions.

A recombinant pBR322 derivative plasmid comprising pBR322 and a DNA fragment that includes the colicin El expression control sequence and the structural gene for colicin inserted into pBR322 at the *Pst*I site of pBR322 is described by Waleh, N.S and Johnson, P.H. (1985), *Proc Acad Sci USA* 82:8389-8393, and is disclosed in International Publication No. W085/01067 This plasmid was used to express a synthetic gene encoding human connective tissue-activating peptide-III U.S. Pat. No. 4,366,246 generally describes recombinant materials and procedures for microbially producing fusion proteins of an exogenous polypeptide linked to an exogenous amino acid sequence via an amino acid that defines a specific cleavage site.

A number of references are cited by Brosius, J. ("Expression Vectors Employing Lambda-, trp, lac-, and lpp-Derived Promoters." Rodriguez, R.L. and Denhardt, D.T., eds. *Vectors A Survey of Molecular Cloning Vectors and Their Uses,* Boston Butterworths; 1988; 207) which support situations wherein fusion of a desired gene to a portion of another gene (for example, lacZ, MS2 polymerase, trpD, trpE, or lambda cI repressor) will result in a more stable hybrid protein product. The cited references do not address low product yield resulting from messenger RNA translational inefficiency.

DISCLOSURE OF THE INVENTION

One aspect of the invention is a method to improve expression of a recombinant protein which method comprises constructing a hybrid gene consisting of a first DNA sequence encoding the amino terminus of said gene, separated by a cleavage site sequence and a second DNA sequence encoding a recombinant protein wherein said hybrid gene encodes a fusion protein, culturing host cells transformed with a vector comprising the hybrid gene, and recovering said fusion protein from the transformed cells wherein the improvement comprises:

selecting a DNA sequence for the first DNA sequence of said hybrid gene, which DNA is of sufficient length to disrupt unfavorable secondary structure formation of the messenger RNA region encoding said recombinant protein and the messenger RNA region containing the ribosome binding site whereby said unfavorable secondary structure formation renders said ribosome binding site inaccessible to ribosomes.

Another aspect of the invention is a plasmid expression vector, which, upon insertion into an *E. coli* bacterium, expresses the product of the fused gene described above in an amount sufficient to provide at least 10% of total cellular protein.

A preferred embodiment of the above-described recombinant plasmid expression vector is Col(150)-PF4, a pBR322 derivative vector comprising pBR322 and a DNA fragment that includes the colicin El expression control sequence and a truncated colicin El structural gene fused to the coding sequence for platelet factor 4.

Another aspect of the invention is a method for the bacterial production of platelet factor 4, which method comprises:

a) culturing *E. coli* transformed with the above-described expression vectors;

b) disrupting the cultured transformants;

c) purifying the fusion protein from other cellular proteins;

d) cleaving the fusion protein at the specific cleavage site; and e) recovering the platelet factor 4 from the cleaved products of step (d).

Still other aspects of the invention are directed to the products of the foregoing methods, particularly the fused Col:PF4 messenger RNA transcripts and gene products and the platelet factor 4 recovered therefrom.

BRIEF DESCRIPTION OF THE DRAWINGS

FIG. 2 is the predicted secondary structure of PF-4 mRNA The legend of FIG. 1 also applies here.

FIG. 5 is an SDS-polyacrylamide gel electrophoresis (PAGE) analysis of cell extracts and demonstrates the expression of several different colicin-PF-4 fusion proteins Lane 1, molecular weight standards; lanes 2 and 3, minus and plus induction of plasmid pNP6:Col(504)-PF-4; lanes 4 and 5, plasmid pNP6:Col(150)-PF-4; lanes 6 and 7, plasmid pNP6:Col(57)-PF-4; lanes 8 and 9, plasmid pNP6:Col(5)-PF-4; lanes 10 and 11, pNP6 PF-4.

MODES OF CARRYING OUT THE INVENTION

The method of the invention comprises PF-4 production in the form of fusion proteins in which the endogenous portion of the protein is a biologically inactive colicin El fragment containing a selective cleavage site within the fusion site such that the desired protein is readily cleavable. Such proteins may be produced using expression vectors in which the PF-4 gene with a suitable translational terminator is inserted into a vector containing the colicin expression control sequence and part of the colicin structural gene at a convenient restriction site near the carboxy terminal end of the colicin structural gene. Due to PF-4's high affinity for glycosaminoglycans, especially to heparins, heparin and chondroitin-sulfate, this property can be used successfully for the affinity chromatographic isolation of the fusion protein and of the free PF-4.

As used herein the term "platelet factor 4" refers to the 70 amino acid protein substantially corresponding to the mature protein described by Poncz et al. (1987), supra, and having any of the biological activities associated with PF-4 such as the afore-described immunostimulatory, chemotactic and heparin neutralization activities.

Modifications to the primary structure itself by deletion, addition, or alteration of the amino acids incorporated into the sequence during translation can also be made without destroying activity of the protein. Such substitutions or other alterations result in proteins having an amino acid sequence which falls within the definition of proteins "having an amino acid sequence substantially equivalent to that of PF-4." For example, residue 47 was correctly identified as being asparagine in the reference by Poncz et al, supra However, this position had been previously characterized in the art as aspartic acid or asparagine, a fact not noted in the literature concerned with PF-4. The present invention has synthesized PF-4 sequences with each residue and determined that each protein has biological activity. Moreover, the protein with aspartic acid$_{47}$ may have more desirable solubility properties.

As is the case for all proteins, the precise chemical structure of the PF-4 protein of the invention depends on a number of factors As ionizable amino and carboxyl groups are present in the molecule, the protein may be obtained as an acidic or basic salt, or in neutral form. All such preparations which retain their activity when placed in suitable environmental conditions are included in the definition of PF-4. Further, the primary amino acid sequence may be augmented by derivatization using sugar moieties (glycosylation) or by other supplementary molecules such as lipids, phosphate, acetyl groups and the like, more commonly by conjugation with saccharides. The primary amino acid structure may also aggregate to form complexes Certain aspects of such augmentation are accomplished through post-translational processing systems of the producing host; other such modifications may be introduced in vitro. Further, individual amino acid residues in the chain may be modified by oxidation, reduction, or other derivatization. Such alterations which do not destroy activity do not remove the protein sequence from the definition.

Various attempts were made to express PF-4 by recombinant DNA techniques, including the direct expression of PF-4 (i.e., not fused to another peptide sequence) in a bacterial host. Using the identical expression systems used for human CTAP-III, significant levels of PF-4 were not obtained. This was surprising in light of the fact that CTAP-III is highly homologous to PF-4 (approximately 75% identical in nucleotide sequence and approximately 65% identical in amino acid sequence). The colicin El expression system described in International Publication No. W085/01067, was found to produce CTAP-III as approximately 30% of the total cellular protein. Using sensitive radio labeling techniques and in vitro transcription-translation assays, it was determined that the low yield of PF-4 protein was a result of poor or inefficient translation of the PF-4 messenger RNA (mRNA) and not a result of poor transcription or protein instability.

Figure 1:
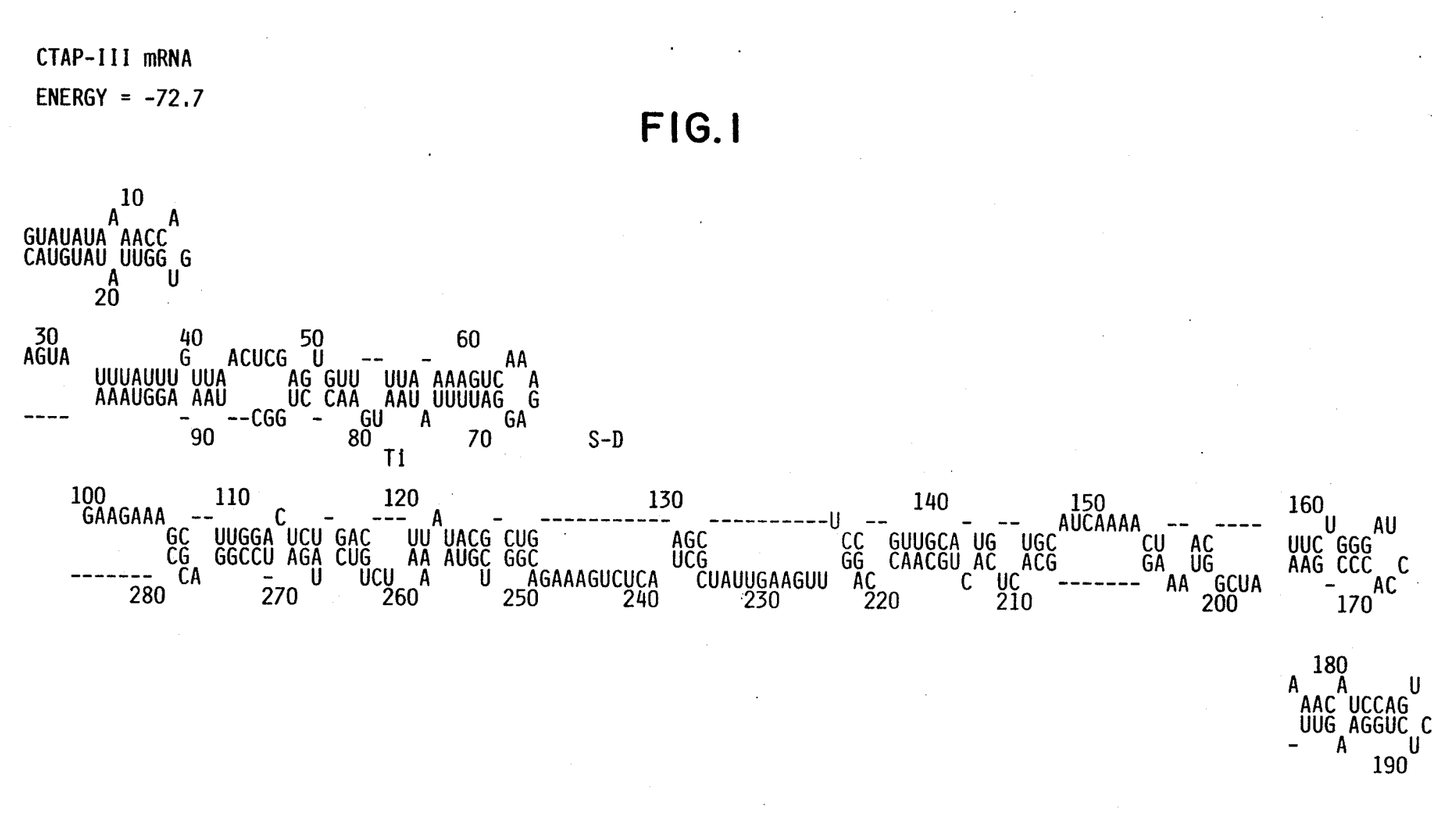
FIG. 1 is the predicted secondary structure of the first 280 nucleotides of the CTAP-III mRNA. S-D designates the ribosome binding site and Ti designates the translation initiation codon (AUG) The S-D and Ti sequences are indicated in bold face type

Experimental studies have shown that expression of a gene is often enhanced when the secondary structure of the mRNA exposes the translation initiation determinants, while a decrease is observed when these regions are masked. Computer methods for predicting the secondary structure of single-stranded nucleic acids were used to predict the structures of both PF-4 and CTAP-III mRNAs according to the method of Zucker, M. and Stiegler, P. (1981) *Nuc Acid Res* 9:133. The results are shown in FIGS. 1 (CTAP-III) and 2 (PF-4). The ribosome binding site of the CTAP-III mRNA is predicted to be exposed in a single-stranded loop, whereas the ribosome binding site of the PF-4 mRNA is predicted to be inaccessible to ribosome binding due to base-pairing with a distant sequence (nucleotides 232–237, FIG. 2).

Generally, it is expected that modifications to the sequence of the mRNA and/or its secondary structure near the ribosome binding site and the AUG initiation codon may affect levels of expression. Thus, when expression levels are low, one skilled in the art generally attempts to modify the nucleotide sequence of the mRNA in the local region consisting of approximately 15 nucleotides on either side of the ribosome binding site, to increase translational efficiency. Until now, it has not been recognized that "global" interactions, that is, long-range interactions between the ribosome binding site and regions of the mRNA outside the local structural region defined above, affect translation efficiencies. The present invention overcomes the problems associated with poor translation of the mRNA by recognizing that unfavorable RNA folding interactions may be disrupted through the insertion of a DNA sequence of sufficient length between the DNA containing the ribosome binding site and the DNA encoding an inefficiently expressed gene thereby creating a hybrid gene which encodes a fusion protein. By sufficient length as used herein, it has been determined that the insert DNA sequence must be greater than 15 base pairs to separate the translational initiation codon and the start of the coding sequence for the recombinant protein. Preferably, this distance is in the range of about 150 to about 450 base pairs.

The fused gene construct is joined with an appropriate expression vector such that the fused gene is flanked at the 5'-end with transcriptional initiation regulatory sequences and at the 3'-end with transcriptional and translational termination sequences. (5'- and 3'- intend the direction of transcription).

After preparing the plasmid DNA for introduction into an appropriate host, the host is transformed, cloned, the clones streaked and individual clones selected for efficient expression by assaying for production of the desired product, e.g., PF-4. As exemplified in the present invention, efficient production means that the level of expression of the PF-4 fusion protein is at least 10% of total cellular protein. Screening can be efficiently performed using Western blots (antibody detection of product) of host cell colonies transferred to filters of nitrocellulose or other suitable material. Alternatively, by analyzing samples using gel electrophoresis an immediate and direct comparison can be made of which clones are most efficiently expressed by visualization of protein staining intensity, autoradiography or Western blotting of the product band. This screening procedure will usually be sufficient, although more quantitative immunoassays or enzyme assays can be employed, as appropriate.

In preferred embodiments of the invention the DNA insert encodes truncated colicin El proteins fused to PF-4. In these embodiments, the colicin El gene encodes a protein which has a hydrophobic segment (approximately 30 amino acids), a physical chemical characteristic which facilitates the purification of the fusion protein from other cellular components This hydrophobic segment allows contaminating proteins to be selectively extracted from the fusion protein using high salt concentrations (such as 1 M guanadinium hydrochloride) and provides colicin El-PF-4 fusion proteins greater than 80% pure.

After the fusion protein is partially purified, PF-4 is separated by subjecting the fusion protein to a chemical or enzymatic reaction that cleaves the protein at the fusion site. For instance, when the two segments of the protein are fused via a methionine residue, the protein may be treated with cyanogen bromide.

The following provides a detailed description of specific embodiments of the invention that involves PF-4, fusion proteins composed of colicin El fragments and PF-4, and the purification of bacterially produced PF-4.

Gene Construction

The synthetic gene for PF-4 consists of 243 base pairs of DNA that are assembled from two major subfragments (designated I and II) composed of eight and four oligonucleotides, respectively. The 12 oligonucleotides were synthesized on an Applied Biosystems DNA Synthesizer using phosphoramidite chemistry.

Figure 3:
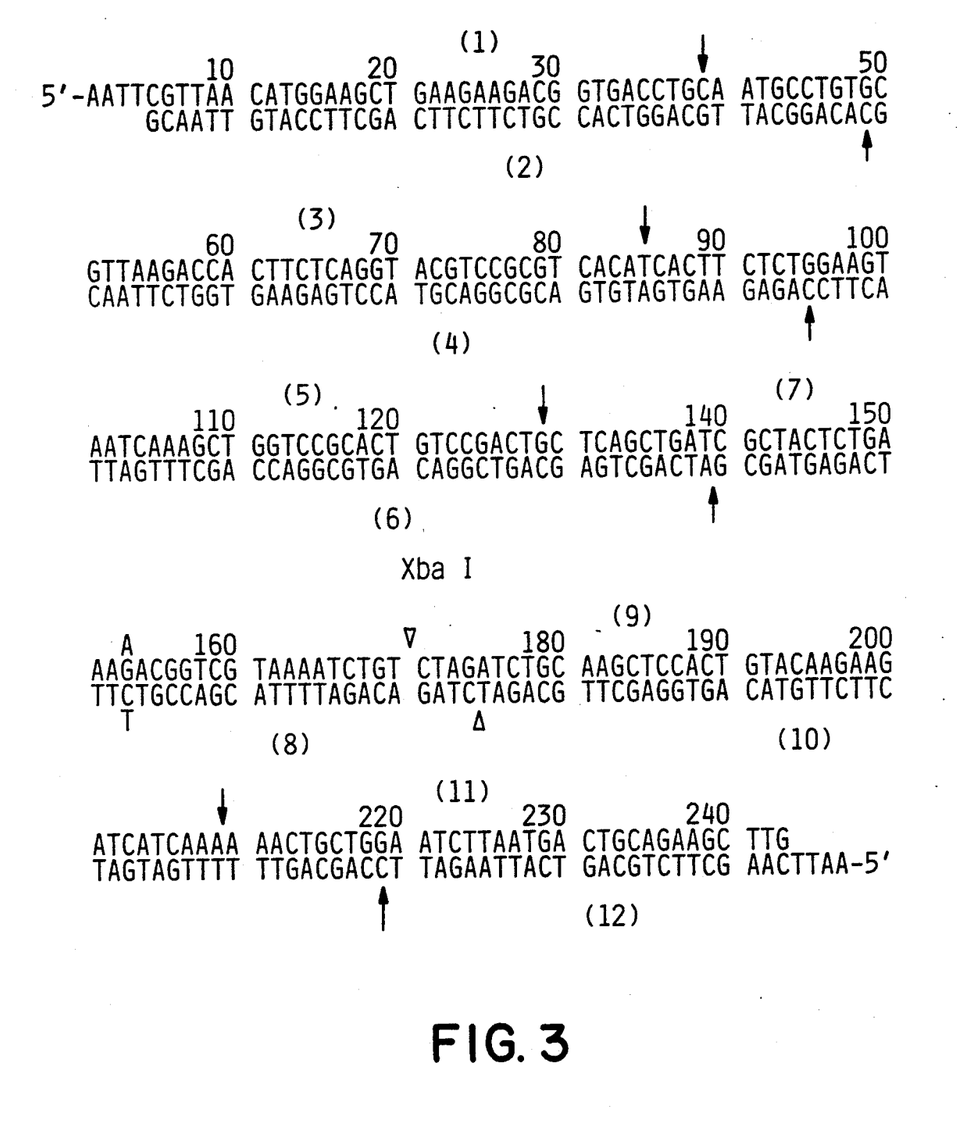
FIG. 3 illustrates the synthetic DNA sequence synthesized for the construction of PF-4 The 12 oligonucleotides used to create the two major fragments, which upon ligation form the entire coding sequence of PF-4, are depicted above the DNA sequence and bounded by the arrows. The single change at nucleotide number 153 specifies either asparagine or aspartic acid at this position.

The 12 synthetic oligonucleotides were purified, characterized, and ligated to produce fragments I and II as described below and as illustrated in FIG. 3.

Oligonucleotide Purification and Characterization

1. Purification

Polyacrylamide gels (12%) were prepared with 7 M urea, 90 mM Tris-borate, and 2 mM EDTA buffer. Sample wells were formed with a comb having teeth at least 2 cm wide. After standing for 3 hours, the gel was pre-electrophoresed for ~30 minutes. Equal volumes of 1 to 5 $A_{260}$ units of the unpurified oligonucleotide sample and 7 M of urea were mixed in 10 mM Tris-HCl buffer, pH. 7.5. The DNA sample was added to the gel, and a dye mixture (0.17% Bromphenol blue, 0.27% xylene cyanol, 10 mM Tris-HCl, pH 7.5) was added to one of the wells to monitor the migration rate of the oligonucleotides. Electrophoresis was performed at 400 to 600 volts until the Bromphenol blue migrated ~30 cm from the top of the gel. Both plates were removed, the gel was wrapped in plastic wrap, and the DNA was placed on a fluorescent background and visualized using shortwave UV light The desired band was carefully cut out using a razor blade The piece of gel was placed in an Eppendorf tube and crushed with a glass bar. Then, 0.5 ml of TE (10 mM Tris-HCl, 1 mM EDTA, pH 7.5) was added to the tube, which was rotated overnight for DNA extraction. The tube was centrifuged at 15,000 rpm for 10 minutes, and the supernatant was recovered. The DNA sample was diluted 10 times with TE and was added to a C-18 Sep-Pak column (prepared using 10 ml of 100% acetonitrile and 20 ml $H_2O$) for desalting. Recovery of DNA was generally between 50 and 80%. The eluate was lyophilized and then resuspended in 0.5 ml $H_2O$.

2. End-Labeling, Gel Electrophoresis, and Autoradiography

Ten pmole of the sample was lyophilized. The dried sample was dissolved in 1 ul of 10×concentrated kinase buffer (700 mM Tris-HCl, pH 7.6, 100 mM $MgCl_2$, 1 mM KCl, 50 mM dithiothreitol), 5 ul $H_2O$, and 1 ul T4 kinase solution containing at least 1 unit of activity. The sample was incubated for 30 minutes at 37° C. After the addition of 5 ul of the dye mixture, the sample was added to a polyacrylamide gel (20%, 0.4 mm thick, 15 cm long), electrophoresed until the Bromphenol blue migrated to the bottom of the gel, and autoradiographed by exposing the gel to X-ray film for 10 to 30 minutes

3. Ligation of Oligonucleotides

Reaction mixtures for ligating oligonucleotides consisted of 50 mM Tris-HCl (pH 7.5), 10 mM MgCl$_2$, 20 mM dithiothreitol, 1 mM ATP, 100 pmole DNA (concentration of 5' ends), and 100 units of T4 ligase in a total volume of 100 ul. The reaction mixtures were incubated overnight at 16° to 21° C.

Ligation reactions were terminated by adding a 3×excess of EDTA to chelate the Mg$^{2+}$. Samples were heat denatured after adding urea and dye mixture and analyzed by gel electrophoresis.

FIG. 3 shows the 12 oligonucleotides used to construct the synthetic gene. Oligonucleotides 1 through 8 composed fragment I and 9 through 12 composed fragment II. These two fragments were assembled in vitro and cloned into the M13 vector as described below to confirm the DNA sequence.

Preparation of M13 Cloning Vector

The double-stranded replicative form (RF) DNA of M13 was prepared as follows 2×YT broth was inoculated with *E. coli* JM101 cells infected by M13 and incubated overnight at 37° C. Cells were collected by centrifugation, washed, resuspended in buffer, lysed with lysozyme and Triton X-100, and treated with ribonuclease. Cellular debris was removed and RF DNA was purified using CsCl-ethidium bromide equilibrium centrifugation. The ethidium bromide was removed using n-butanol extraction. RF DNA was dialyzed and concentrated using ethanol precipitation.

Transformation System

Preparation of Competent Cells

*E. coli* was cultured in 2×YT broth until the OD$_{660}$ was between 0.6 and 0.7. Cells were collected by centrifugation, resuspended in 50 mM CaCl$_2$ (half of the culture volume), and kept on ice for 20 minutes. Cells were collected and resuspended in 1/10 volumes of CaCl$_2$.

Transformation

M13 RF DNA, which had been previously digested with endonucleases EcoRI and XbaI was ligated with the PF-4 fragments I or II and was mixed with competent JM101 cells and kept on ice for 20 to 40 minutes The mixture was heat-shocked at 46° C. for 2 minutes and mixed with IPTG, Bluo-gal, soft agar (46° C.), and fresh growing JM101 cells. The mixture was plated on YT agar plates and incubated overnight at 37° C.

The JM101 cells that were transformed by intact M13 synthesized beta-galactosidase and produced blue plaques. Cells that were transformed by M13 containing a PF-4 fragment did not make beta-galactosidase and produced colorless plaques.

Nitrocellulose Filter Hybridization

The recombinant phage were screened for the presence of the PF-4 gene sequence as follows. Phage cultures were dot-blotted onto nitrocellulose filter paper using a BRL (Bethesda Research Laboratories) 96-well HYBRI-DOT® manifold The blotted phage were lysed, and the DNA was denatured and immobilized by washing the filters once with agitation for 15 minutes each in the following solutions: 0.5 M NaOH; 0.5 M Tris, pH 7.4; 2×SSC (0.3 M NaCl, 30 mM sodium citrate), pH 7. Filters were washed briefly in 95% ethanol, air-dried, prehybridized for three hours, and hybridized overnight with $^{32}$P-labeled oligonucleotide at room temperature. Hybridized filters were washed twice in 1×SSPE with 0.1% SDS at 25° C. for 15 minutes each, dried, and autoradiographed. Then the filters were rewashed and probed with oligonucleotide 5'-GTAAAATCTGTCTAGACCTG-3', which corresponds to the junction between the PF-4(I) and PF-4(II) subfragments.

Isolation of ColEl Plasmid

Strain JC411 (Col EL-D30) was grown in 60 liters of M9 medium (per liter: 1 g NH$_4$Cl, 6 g Na$_2$HPO$_4$·H$_2$O, 3 g KH$_2$PO$_4$, 5 g NaCl, 3 g casamino acids, 1 ml 10% MgSO$_4$ supplemented with 10 ml 20% glucose and 0.5 ml 1 M CaCl$_2$ added after autoclaving) in a fermenter at 37° C. to a cell density of approximately 5×10$^8$ CFU/ml. Chloramphenicol was added to a final concentration of 100 ug/ml, and the incubation at 37° C. was continued for another 6 hours Cells were recovered using a Sharpels continuous-flow centrifuge. Ten g (wet weight) of the pellet was suspended in 180 ml of 50 mM Tris-HCl buffer (pH 8.0) containing 50 mM EDTA and 15% sucrose Then, 0.14 g of lysozyme was added, and the mixture was allowed to stand at room temperature for 10 minutes. Next, 16 ml of 10% SDS and 20 ml of 5 M potassium acetate were added. The mixture was incubated on ice for 30 minutes and then centrifuged at 12,000 rpm for 30 minutes using the SS-14 rotor and a Sorvall centrifuge Four mg of pancreatic ribonuclease A was added to the supernatant and the mixture was incubated at 37° C. for 1 hour. The sample was extracted twice with an equal volume of phenol saturated with 0.1 M Tris, pH 8.0, and the DNA was precipitated by adding 1/10 sample volume of 3.0 M sodium acetate and 2.5 volumes of cold ethanol, followed by an overnight incubation at −20° C. The resulting precipitate was recovered by centrifugation at 7,000 rpm for 50 minutes in a refrigerated Sorvall centrifuge using an HB-4 rotor. The pellet was dissolved in 50 ml of 10 mM Tris-HCl buffer (pH 7.5) containing 0.3 M NaCl and 5 mM EDTA (NE buffer). This sample was then applied to a Bio-Gel A.5 column (Bio-Rad Laboratories, Richmond, Calif.), 5×100 cm, equilibrated with NE buffer. The DNA was eluted with NE buffer. Twenty-ml fractions were collected at a flow rate of 60 ml/hr. The elution of DNA was monitored by measuring the absorbance of each fraction at 260 nm using a Gilford 2600 UV-VIS spectrophotometer. The host DNA and the plasmid DNA were recovered together in the void volume. The fractions containing the DNA were pooled and precipitated with ethanol. The precipitate was collected by centrifugation at 8,000 rpm for 40 minutes in a refrigerated Sorvall centrifuge using an HB-4 rotor and redissolved in 5 ml 10 mM Tris-HCl buffer (pH 7.8) containing 0.2 M NaCl.

The DNA sample was applied to an RPC-5 column, 0.9×90 cm, and packed under pressure at 30° C. The DNA was eluted with a linear gradient (total volume, 1 liter) of 0.6–0.7 M NaCl in 10 mM Tris-HCl buffer, pH. 7.8. Fractions of 2.5 ml were collected at a flow rate of 0.8 ml/min. The elution of DNA was monitored by measuring the conductivity of each collected sample using a conductivity meter (Radiometer, Copenhagen), and by agarose gel electrophoresis using vertical agarose slab gels (0.25×14×15.5 cm). The samples were applied to 1% agarose gels prepared in 40 mM Tris base buffer, pH 8.2, containing 1 mM EDTA and 5 mM sodium acetate (TAE buffer), and electrophoresed for 3 hours at a constant applied voltage of 5 V/cm. Fractions containing the supercoiled and the nicked circular DNA were pooled separately and were precipitated with cold ethanol. The resulting precipitates of ColE1 DNA molecules were dissolved in 1.0 and 0.6 ml TEN buffer, respectively.

Isolation of Plasmid pBR322

Plasmid pBR322 was isolated from *E. coli* strain 294 (pBR322) by the procedure used for isolating ColE1 plasmid described above.

Preparation of Sheared Fragments of ColE1 DNA

Two hundred ul of nicked circular ColE1 DNA (0.7 ug/ul) and 2.8 ml of 0.3 M sodium acetate were mixed. The DNA solution was placed in the microhomogenizer cell of an omnimixer (Dupont Instruments, Newton, Conn.), and the DNA was sheared at 38,500 rpm for 20 min. The temperature was kept at 0° C. throughout the shearing process The sheared DNA was precipitated with ethanol, redissolved in 100 ul of TEN buffer, and treated with calf intestinal phosphatase (CIT) (Boehringer Mannheim, Indianapolis, Ind.). The treatment with CIT was carried out in two 500 ul reaction mixtures. Each reaction mixture contained 380 ul distilled water, 50 ul 1 M Tris-HCl buffer (pH 8.0), 5 ul 10 MM zinc sulfate, 5 ul CIT (10 U/ul). After incubation at 37° C. for 30 minutes, an additional 5 ul of CIT was added and the incubation at 37° C. continued for another 30 minutes. The reaction mixtures were extracted twice with an equal volume of buffer-saturated phenol, and the DNA was precipitated with ethanol. The heterogeneous population of DNA fragments was further purified and separated according to size by sucrose gradient velocity centrifugation. A discontinuous sucrose gradient was prepared by sequential layering of 3.4 ml of 20%, 15%, 10%, and 5% sucrose in 0.3 M sodium acetate buffer (pH 7.0) containing 1 mM EDTA in centrifuge tubes for the SW40 rotor (Beckman). The DNA sample in 100 ul (0.25 ug/ul) was layered on the sucrose gradient and centrifuged at 35,000 rpm for 20 hours at 10° C. using an L8-70 Beckman ultracentrifuge. Fractions of 0.5 ml each were collected and precipitated with ethanol. The precipitates were redissolved in 50 ul of TEN buffer and analyzed by agarose gel electrophoresis. DNA fragments generated by the treatment of bacteriophage DNA with HindIII endonuclease were used as molecular-weight standards. The lambda/HindIII reaction mixture contained 27 ul distilled water, 10 ul 5×HindIII buffer, 1 ul lambda DNA (0.7 ug/ul), and 2 ul HindIII solution (2 U/ul).

Sucrose gradient fractions, containing sheared ColE1 DNA fragments averaging 2,000 bp, were pooled, precipitated with ethanol, and redissolved in TEN buffer.

Cloning of Sheared ColE1 Fragments in pBR322

Plasmid pBR322 was cleaved to linear molecules with PstI. The reaction mixture contained 520 ul distilled water, 200 ul 5×PstI buffer, 200 ul pBR322 DNA solution (0.25 ug/ul), and 80 ul PstI (12 U/ul), and was incubated at 37° C. for 4 hours. The reaction was stopped by adding EDTA to 20 mM and extracted with an equal volume of phenol. The DNA was precipitated with ethanol and redissolved in TEN buffer.

Poly(dG) homopolymer extensions were added to linear pBR322 molecules in a reaction mixture containing 5 ul distilled water, 20 ul 500 mM potassium cacodylate, 10 ul 10 mM cobalt chloride, 10 ul 1 mM DTT, 2 ul 10 mM dGTP, 20 ul $^3$H-dGTP (New England Nuclear Corporation), 25 ul DNA (0.04 ug/ul), and 5 ul (12 U/ul) terminal deoxynucleotidyl transferase (Bethesda Research Laboratories, Inc., Gaithersburg, Md.).

Poly(dC) homopolymer extensions were added to ColE1 sheared fragments in a similar reaction mixture, except that the total DNA was 2.0 ug and the nucleotide triphosphate was dCTP. The above reactions were carried out at 37° C. for 2 and 3 minutes, respectively, and were stopped by adding EDTA to 20 mM and extracting with phenol. ColE1-[poly(dC)] fragments were redissolved in 115 ul distilled water and were annealed to linear pBR322-[poly(dG)] molecules by adding 40 ul 0.5 M NaCl, 40 ul 50 mM EDTA (pH 7.25), and 3 ul linear pBR322-[poly(dG)] DNA solution (0.1 ug/ul). The annealing mixture was incubated at 70° C. for 15 minutes and then cooled to 40° C. over a 5-hour period. The mixture was kept at 45° C. overnight, then cooled to room temperature.

For transformation into *E. coli* 294, an overnight culture growth in L-broth was diluted 1:100 into fresh L-broth medium and incubated with shaking at 37° C. until the OD$_{600}$ was 0.6. At this time, 35 ml of culture was centrifuged at 6,000 rpm for 120 minutes at 4° C., and the pellet was resuspended in 20 ml 0.05 M CaCl$_2$. The cells were incubated on ice for 15 minutes before they were collected by centrifugation at 4,000 rpm for 10 minutes. The cells were resuspended in 4 ml 0.05 M CaCl$_2$ and mixed with 200 ul of a DNA solution prepared by adding 50 ul of the annealing mixture and 150 ul 10 mM Tris-HCl (pH 7.5) containing 10 mM MgCl$_2$ and 10 mM CaCl$_2$. This mixture was incubated at 0° C. for 25 minutes, followed by incubation at 50° C. for 10 seconds and at room temperature for 10 minutes. At this point, 14 ml of L-broth was added and the culture was shaken at 37° C. for 30 minutes Then, 80 ul of tetracycline solution, 1.25 mg/ml, was added to the culture, and the incubation was continued for another 30 minutes. Aliquots of 100 ul were plated on freshly prepared agar plates containing 25 ml L-broth, 1.5% agar and 25 ug/ml tetracycline. The tetracycline resistant (Tc$^r$) transformants were further tested for sensitivity to ampicillin (Ap$^s$) by plating on agar containing 25 ug/ml ampicillin.

The Tc$^r$ Ap$^s$ transformant colonies were then screened for the spontaneous production of colicin. Single colonies were spotted on L-agar plates and were incubated at 37° C. overnight. The colonies were killed by exposing them to chloroform vapor, then overlaid with 5 ml L-broth containing 0.7% agar and 0.1 ml of an overnight culture of *E. coli* K-12, CL142. After the agar was allowed to harden, the plates were incubated at 37° C. overnight. Colonies with a zone of inhibition around them were scored as colicin producers (Col+).

The Tc$^r$ Ap$^s$ Col+ transformant colonies were screened for the presence of recombinant plasmids by analyzing a small amount of cleared lysate by agarose gel electrophoresis. The size of the plasmids was determined by measuring the electrophoretic migration of DNA through an agarose gel using 8 plasmid standards, ranging in size from $1.36 \times 10^6$ to $35.8 \times 10^6$ daltons (Marcina, F.L., et al. (1978), *Plasmid* 1:417–420).

Restriction Endonuclease Fragment-Size Analysis of Recombinant Plasmids

Transformed clones were grown in 2-liter cultures. Cleared lysates were prepared as described above. The supernatants were treated with pancreatic RNase A (100 ug/ml at 37° C. for 30 minutes) and then were extracted with phenol. The DNA was precipitated with ethanol and redissolved in TEN buffer.

Restriction enzymes were obtained as commercial preparations from Bethesda Research Laboratories, Inc. (BRL). The DNA was digested with PstI, EcoRI, SmaI, and SacII, using the conditions specified by BRL. Samples were applied to 1% agarose gels and electrophoresed for 4 hours at a constant applied voltage of 5 V/cm. The molecule weights of restriction fragments were determined relative to the standard migration patterns of bacteriophage lambda DNA digested with HindIII and HaeIII.

Figure 4:
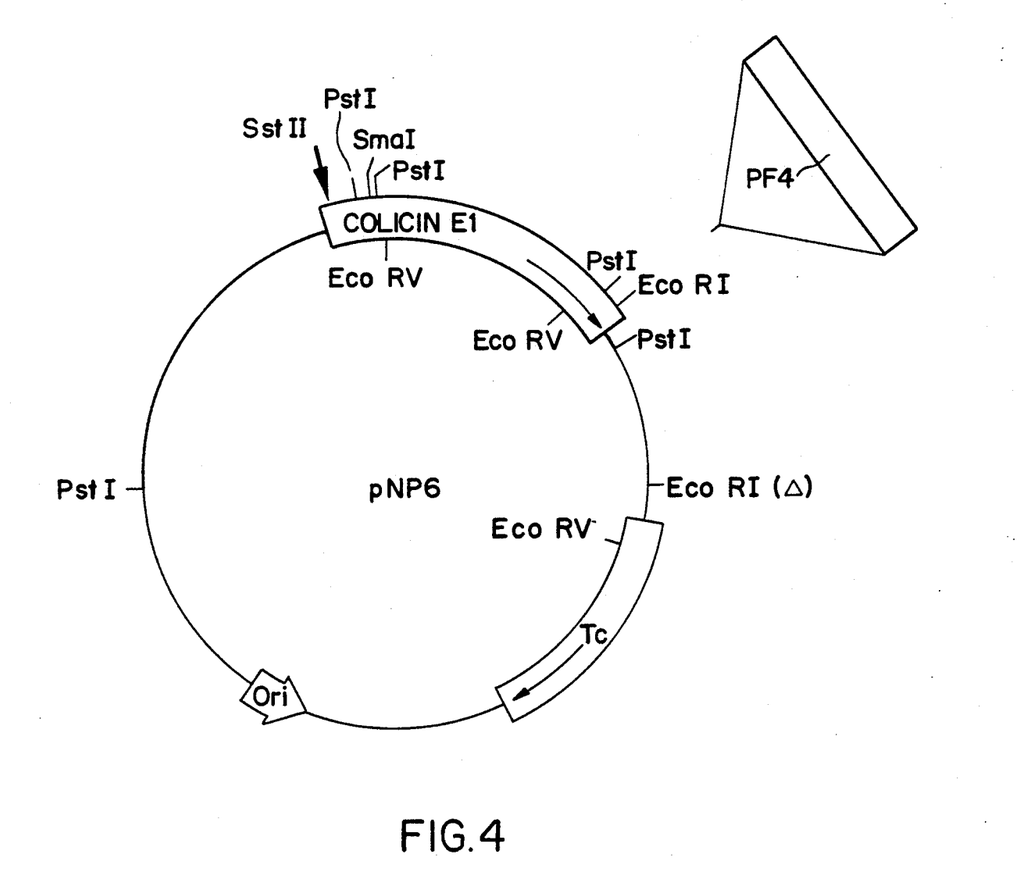
FIG. 4 is a restriction site and function map of plasmid pNP6-deltaEcoRI that is used in making an expression vector containing the synthetic gene of FIG. 2.

Restriction analysis using PstI was used to establish the size of the fragment inserts in the PstI site of the pBR322 portion of the recombinant plasmids. FIG. 4 is a restriction map of the recombinant plasmid, designated pNP6, of one of the transformed clones. A sample of this transformed clone, designated NP6-294, was deposited in the ATCC on 24 August 1983. This sample was assigned ATCC accession no. 39418. This deposit was accepted under the Budapest Treaty and will be maintained and made accessible to others in accordance with the provisions thereof.

E. coli strain NP6-294 (pNP6) was grown and plasmid DNA was further purified by adjusting 500 ug of DNA to 3.9 ml of TEN buffer and adding 3.45 g CsCl and 0.1 ml ethidium bromide stock solution (5 mg/ml). The mixture was transferred into a cellulose nitrate tube for an SW50.1rotor (Beckman) and centrifuged at 36,000 rpm at 10° C. for 40 hours. The plasmid DNA band was located under a longwave UV light and was removed with a syringe by puncturing the tube from the side. The DNA sample was extracted five times with butanol and dialyzed against 100 volume (×3) of TEN buffer for 24 hours at 4° C. The DNA was then precipitated with 2.5 volumes of ethanol and 1/10 volume of 3 M sodium acetate.

Preparation of Derivative pNP6deltaRI

Plasmid pNP6 contains two EcoRI restriction sites, one located in the carboxy terminal region of the colicin E1 gene, the other located near the tetracycline resistance gene of the original pBR322 vector. A derivative of pNP6 lacking the second site was constructed as follows. pNP6 was digested with EcoRI under limited reaction conditions so that linear molecules (cleaved at only one of the two sites) were produced. Linear molecules of pNP6 were purified by agarose gel electrophoresis and subsequently reacted with DNA polymerase I and deoxyribonucleotide triphosphates to fill in the single-stranded ends. The resulting molecules were circularized in a blunt-end ligation reaction using T4 ligase and then they were used to transform E. coli 294 as described previously.

Colicin-producing transformants were selected as described previously. DNA was isolated from individual clones and digested with EcoRI to identify those that contained a single, intact EcoRI site within the colicin gene. The location of the single EcoRI site was confirmed by additional restriction endonuclease mapping.

Preparation of pNP6-Col(504)-PF4

The synthetic PF-4 gene was removed from the M13 sequencing vector and cloned into the single EcoRI site of plasmid pNP6deltaRI. This recombinant DNA plasmid, illustrated in FIG. 4 and designated pNP6-Col(504)-PF4, has the ability to produce a large protein (574 amino acids) that is a fusion of the PF-4 protein (70 amino acids) with residues 1–504 of the colicin gene. Cells containing this plasmid were grown in culture and treated with mitomycin C to induce synthesis of the fusion protein.

Small-scale experiments (FIG. 5, lanes 2 and 3) demonstrated that the fusion protein was produced as approximately 10 to 20% of the total cellular protein. However, purification and characterization of the CNBr-cleavage products from the PF-4 fusion protein by heparin-affinity chromatography was not reproducible due to incorrect disulfide bond formation and interference of the colicin fragments. Poor yield was also associated with larger culture volumes (for example, 12-liter batches) due to possible instability of this plasmid construction.

Preparation of pNP6-Col(150)-PF4

Major improvements in the yield of active, correctly folded PF-4 protein were achieved by reducing the size of the colicin segment. A medium-sized fusion gene was constructed from pNP6-Col(504)-PF4 by deleting approximately 1,000 base pairs of DNA under partial EcoRV digestion conditions. There are three EcoRV restriction sites in pNP6-Col(504)-PF4; two are within the colicin E1 structural gene and the other is within the tetracycline gene as illustrated in FIG. 4. Since transformants are selected for Tc$^r$, only the desired transformants having the EcoRV fragment deleted from the colicin gene will result. The resulting plasmid, designated Col(150)-PF4, codes for only 150 amino acids of colicin preceding the PF-4 coding sequence, and contains a single methionine residue joining the colicin segment and PF-4. The fusion of this colicin segment to the PF-4 protein specifically enhances the recovery and purification procedure.

E. coli 294 cells containing plasmid pNP6-Col(150)-PF4 were reproducibly cultured in volumes (up to at least 12 liters) and upon induction with mitomycin C, produced the Col(150)-PF4 medium fusion as approximately 20% of the total cellular protein.

Preparation of pNP6-Col(57)-PF4

The size of the colicin fusion peptide was reduced further to a 57 amino acid segment by deleting the region between the SstII and the EcoRV restriction sites in plasmid pNP6-Col(150)-PF4. Purified pNP6-Col(150)-PF4 DNA was cleaved to linear molecules with SstII restriction enzyme and then treated with T4 DNA polymerase and dCTP, conditions under which the 3' to 5' exonuclease activity of the polymerase converted the SstII-generated ends of the plasmid DNA to blunt-ends. The product DNA of this reaction was cleaved with EcoRV restriction enzyme and the resulting large DNA fragment was purified, converted to circular DNA in a DNA ligase reaction and then used to transform cells as described for pNP6-Col(150)-PF4. The resulting plasmid, designated pNP6-Col(57)-PF4, codes for 57 amino acids of colicin preceding the PF-4 coding sequence, and contains a single methionine residue joining the colicin segment and PF-4.

Purification of PF-4

Protein extracts were prepared from pNP6-Col(150)-PF4 by sonication of induced cells in 1 M guanidinium hydrochloride (GnHCl) or 25 mM Tris, 10 mM EDTA, 50 mM glucose, pH 8.0 (TEG). The fusion protein was found in the insoluble fraction Following solubilization of the PF-4 fusion protein in 7 M urea or 6 M GnHCl, a sample of the protein was dialyzed extensively against distilled water in preparation for the CNBr cleavage reaction. The fusion protein precipitated during dialysis and was collected by centrifugation. The precipitate was lyophilized and then dissolved in 70% formic acid and reacted with a 100 to 1,000-fold molar excess of CNBr for 18 hours at room temperature.

The CNBr reaction mixture was lyophilized, resuspended in distilled water and lyophilized again. The protein mixture was dissolved in 0.05 M Tris buffer, pH 8.2 containing 6 M GnHCl. A reducing agent such as dithiothreitol or beta-mercapthoethanol was added to a final concentration of approximately 0.1 M, and the mixture was incubated at a temperature between 20° and 370° C. for 1 to 4 hours. The resulting solution was then dialyzed against the same buffer but without reducing agent. The protein solution was adjusted to a PF-4 concentration of approximately 0.2 mg/ml and a 2:1 mixture of oxidized and reduced glutathionine at a final concentration of 1 mM. The protein refolding reaction was allowed to proceed at room temperature for 10 to 20 hours, during which time it was dialyzed against 10 to 50 volumes of 0.05 M Tris buffer, pH 8.2 containing 0.5 M NaCl. These conditions result in greater than 80% of the PF-4 forming the correct disulfide bonds and refolding to the native conformation.

Heparin-Affinity Chromatography

The refolding mixture was subsequently dialyzed against distilled water and lyophilized. The protein was then dissolved in GnHCl or NaCl or chondroitin sulfate at high concentration (>10 mg/ml protein), and diluted to an ionic strength of 0.2-0.4 just prior to purification by heparin affinity chromatography. Chromatographic columns were prepared using commercially available heparin agarose (BioRad). Heparin may be substituted with other glycosaminoglycans such as chondroitin sulfate. Thus, as used herein, the use of the term "heparin" includes related compounds.

Protein was applied to the column in low ionic strength buffer at pH 6.5 and the column was eluted with a linear gradient of NaCl. Native recombinant PF-4 eluted at a NaCl concentration between 1.2 and 1.4 M, which is the position for human, platelet-isolated PF-4. Unfolded or incorrectly folded PF-4 eluted at a significantly lower NaCl concentration, usually 0.7 M NaCl or less.

Recombinant PF-4 prepared using this procedure was indistinguishable from human PF-4 as characterized by reverse phase-HPLC, amino terminal sequence, amino acid composition and reactivity against human PF-4 antisera.

Formulations for Therapeutic Use

The purified PF-4 protein will typically be formulated with conventional pharmaceutically acceptable carriers for administration to humans for example, to stimulate wound healing. It may be administered topically at the desired site conventional topical formulations such as creams, pastes, gels, sprays, ointments, and salves. Carriers used in such formulations are well known and include, without limitation, petrolatum, polyethylene glycol, gelatin, isopropyl myristate, polyvinyl alcohol, and the like. Alternatively, the purified PF-4 protein may be administered using controlled release dosage forms which typically consist of bandages or skin patches that contain the PF-4 in a manner such that it is released at a controlled rate to the skin. The control mechanism may be diffusion, osmosis, dissolution, erosion, or iontophoresis. The topical formulation of PF-4 may contain minor amounts of additives such as emollients, stabilizers, surfactants, skin penetration altering agents, and pigments. The concentration of PF-4 in the formulation will be correlated to the prescribed dose and surface area being treated. The concentration will normally be in the range of 0.0001% to 1% by weight of the dosage form. In any event, the amount administered is sufficient to produce the desired pharmacological effect, e.g., chemotaxis, etc., so as to facilitate wound healing.

The purified PF-4 protein may also be formulated for application as a tumor inhibitor and used in vitro or in vivo for reducing the rate of neoplastic cell growth, particularly carcinomas and sarcomas of the lung, breast, skin, etc. The PF-4 formulations can be administered to a host suspected of having neoplasia by applying the PF-4 formulations to a neoplastic site to reduce the rate of proliferation. Methods of application may include local and systemic administration, including injection, introduction by catheter or the like.

Systemic formulations are generally known in the art and include formulation in buffer or physiological saline, or other appropriate excipients. Dosage will vary depending upon whether it is systemic or local, with dosage concentrations generally being from about 0.1 ug to 1,000 ug/Kg and total dosages for large mammals including humans of from about 0.01 to 10 mg per treatment dose.

Modifications of the above-described modes for carrying out the invention that are obvious to those of skill in the technical fields related to the invention are intended to be within the scope of the following claims. For instance, it is also within the scope of the invention to incorporate the colicin El regulatory and structural gene sequences into plasmids other than pBR322 that have suitable replicatory and marker functions and suitable restriction sites.

I claim:

1. In a method to improve expression of platelet factor 4 which method comprises constructing a hybrid gene consisting of a first DNA sequence encoding the amino terminus of said hybrid gene, separated by a cleavage site sequence, and a second DNA sequence encoding platelet factor 4, culturing host cells transformed with a vector comprising the hybrid gene, and recovering said fusion protein from the transformed cells wherein the improvement comprises:

selecting a colicin El structural gene sequence for the first DNA sequence of said hybrid gene, which DNA is in the range of 15 to about 450 basepairs in length, sufficient to disrupt secondary structure formation between messenger RNA encoding platelet factor 4 and the messenger RNA region containing the ribosome binding site whereby said secondary structure formation renders said ribosome binding site inaccessible to ribosomes.

2. The method of claim 1 wherein the DNA sequence for the first DNA sequence is in the range of about 150 to about 450 base pairs.

3. The method of claim 1 wherein the carboxy terminus of the colicin El structural gene is truncated at the EcoRI restriction site.

4. The method of claim 1 wherein platelet factor 4 has the DNA sequence shown in FIG. 3.

5. The method of claim 1 wherein at least 10% of total cellular protein is the fusion protein.

6. The method of claim 3 wherein the truncated colicin El structural gene is further modified by removing the internal EcoRV restriction fragment.

7. The method of claim 6 wherein the colicin El structural gene is further modified by removing the SstII/EcoRV restriction fragment.

8. The method of claim 1 wherein the first DNA sequence encodes a hydrophobic polypeptide which aids in the purification of said fusion protein.

9. A recombinant composite messenger RNA of claim 1 comprising a sequence specifying a ribosome binding site, a first RNA sequence encoding the colicin El structural gene, including a translation initiation codon, and a second RNA sequence encoding the recombinanat protein.

10. The messenger RNA of claim 9 wherein the second RNA sequence encodes platelet factor 4.

11. A recombinant expression vector for the microbial production of platelet factor 4 comprising:
  a) a colicin El expression control sequence having a promoter, operator, ribosome binding site, initiation codon and transcriptional terminator;
  b) a DNA fragment encoding a gene fusion consisting of 15 to about 450 basepairs of the colicin El structural gene, a specific cleavage site, and the platelet factor 4 gene; and
  c) a bacterial origin of replication.

12. A plasmid expression vector according to claim 11 wherein said vector, when inserted into a bacterium, expresses the fused gene product in an amount sufficient to provide at least 10% of total cellular protein.

13. A plasmid expression vector according to claim 11 wherein the internal EcoRV restriction fragment of the colicin El structural gene is removed.

14. A plasmid expression vector according to claim 11 which is pNP6-Col(150)-PF4.

15. A plasmid expression vector according to claim 11 which is pNP6-Col(57)-PF4.

16. *E. coli* transformed with the plasmid expression vector of claim 11.

17. A fused gene product according to claim 11.

18. The fused gene product according to claim 17 which is Col(150)-PF4.

19. The fused gene product according to claim 17 which is Col(57)-PF4.

20. A method for the bacterial production of platelet factor 4, which method comprises:
  a) culturing the *E. coli* transformants of claim 12;
  b) disrupting the transformants;
  c) purifying the fusion protein from other cellular proteins;
  d) cleaving the fusion protein at the specific cleavage site; and
  e) recovering the platelet factor 4 from the cleaved product of step (d).

21. The method of claim 20 wherein the transformants are disrupted using 1 M guanidinium hydrochloride or 25 mM Tris, 10 mM EDTA, 50 mM glucose, pH 8.0.

22. The method of claim 21 wherein the fusion protein is purified by extraction of insoluble protein using solutions of 6 M guanidinium hydrochloride or 7 M urea.

23. The method according to claim 20 wherein the specific cleavage site is a methionine which is cleaved with cyanogen bromide.

24. The method according to claim 20 wherein platelet factor 4 is purified by heparin affinity chromatography.

* * * * *